(12) United States Patent
Boctor et al.

(10) Patent No.: US 9,636,083 B2
(45) Date of Patent: May 2, 2017

(54) HIGH QUALITY CLOSED-LOOP ULTRASOUND IMAGING SYSTEM

(71) Applicant: The Johns Hopkins University, Baltimore, MD (US)

(72) Inventors: Emad M. Boctor, Baltimore, MD (US); Xiaoyu Guo, Baltimore, MD (US); Ralph Etienne-Cummings, Baltimore, MD (US); Pezhman Forought, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 535 days.

(21) Appl. No.: 13/943,649

(22) Filed: Jul. 16, 2013

(65) Prior Publication Data

US 2014/0024928 A1    Jan. 23, 2014

Related U.S. Application Data

(60) Provisional application No. 61/672,524, filed on Jul. 17, 2012.

(51) Int. Cl.
*A61B 8/00* (2006.01)
*A61B 8/08* (2006.01)
(Continued)

(52) U.S. Cl.
CPC .............. *A61B 8/0841* (2013.01); *A61B 1/00* (2013.01); *A61B 8/12* (2013.01); *A61M 25/00* (2013.01);
(Continued)

(58) Field of Classification Search
CPC ....... A61B 8/54; A61B 8/4488; A61B 8/5223; A61B 8/485; A61N 7/02; A61N 2007/0052; A61N 2007/0095
See application file for complete search history.

(56) References Cited

U.S. PATENT DOCUMENTS 6,719,700 B1    4/2004    Willis
7,068,867 B2    6/2006    Adoram et al.
(Continued)

FOREIGN PATENT DOCUMENTS

EP             1312310 A2     5/2003
WO       WO-99/58060 A1    11/1999
(Continued)

OTHER PUBLICATIONS

International Search Report issued in PCT. Application No. PCT/US2013/050757 dated Nov. 22, 2013.
(Continued)

*Primary Examiner* — Joel Lamprecht
(74) *Attorney, Agent, or Firm* — Venable LLP; Henry J. Daley; Laura G. Remus

(57) ABSTRACT

A closed-loop ultrasound system includes an ultrasound receiver, an ultrasound transmitter at least one of integral with or at a predetermined position relative to the ultrasound receiver, and a trigger circuit configured to receive detection signals from the ultrasound receiver and to provide trigger signals to the ultrasound transmitter in response to received detection signals. The ultrasound transmitter is configured to transmit ultrasound energy in response to the trigger signals.

36 Claims, 15 Drawing Sheets

(51) Int. Cl.
*A61B 1/00* (2006.01)
*A61M 25/00* (2006.01)
*A61B 8/12* (2006.01)
*A61N 7/02* (2006.01)
*A61B 5/00* (2006.01)
*A61B 8/14* (2006.01)
*A61B 18/00* (2006.01)
*A61B 6/03* (2006.01)
*A61B 6/00* (2006.01)
*A61B 8/15* (2006.01)
*A61B 10/02* (2006.01)
*A61B 18/14* (2006.01)
*A61B 34/20* (2016.01)
*A61B 90/00* (2016.01)

(52) U.S. Cl.
CPC ............ *A61N 7/022* (2013.01); *A61B 5/0095* (2013.01); *A61B 5/4836* (2013.01); *A61B 6/037* (2013.01); *A61B 6/425* (2013.01); *A61B 8/14* (2013.01); *A61B 8/15* (2013.01); *A61B 8/4494* (2013.01); *A61B 8/52* (2013.01); *A61B 10/02* (2013.01); *A61B 18/00* (2013.01); *A61B 18/1492* (2013.01); *A61B 2018/00982* (2013.01); *A61B 2034/2063* (2016.02); *A61B 2090/378* (2016.02)

(56) References Cited

U.S. PATENT DOCUMENTS

| | | | | |
|---|---|---|---|---|
| 2006/0184042 A1* | 8/2006 | Wang | ............ | A61B 5/0073 600/476 |
| 2010/0168572 A1* | 7/2010 | Sliwa | ............ | A61B 8/0833 600/439 |
| 2010/0268042 A1* | 10/2010 | Wang | ............ | A61B 5/0059 600/322 |
| 2011/0201914 A1* | 8/2011 | Wang | ............ | A61B 5/0059 600/407 |
| 2013/0338478 A1* | 12/2013 | Hirota | ............ | A61B 8/429 600/407 |

FOREIGN PATENT DOCUMENTS

| | | |
|---|---|---|
| WO | WO-03/022156 A1 | 3/2003 |
| WO | WO-2004/021044 A1 | 3/2004 |
| WO | WO-2004/060168 A1 | 7/2004 |
| WO | WO-2004/086082 A1 | 10/2004 |
| WO | WO-2010/020939 A2 | 2/2010 |
| WO | WO-2011/138698 A1 | 11/2011 |
| WO | WO-2012/024201 A1 | 2/2012 |

OTHER PUBLICATIONS

Breyer et al., "Ultrasonically marked catheter—a method for positive echographic catheter position identification," Medical Image Computing and Computer-Assisted Intervention (MICCAI) 1984, vol. 22, pp. 268-271.

Mung et al., "A non-disruptive technology for robust 3D tool tracking for ultrasound-guided interventions," Medical Image Computing and Computer-Assisted Intervention (MICCAI) 2011, vol. 6891, pp. 153-160.

* cited by examiner

HIGH QUALITY CLOSED-LOOP ULTRASOUND IMAGING SYSTEM

CROSS-REFERENCE OF RELATED APPLICATION

This application claims priority to U.S. Provisional Application No. 61/672,524, filed Jul. 17, 2012, the entire contents of which are hereby incorporated by reference.

BACKGROUND

1. Field of Invention

The field of the currently claimed embodiments of this invention relates to ultrasound systems, and more particularly to closed-loop ultrasound system.

2. Discussion of Related Art

Ultrasound imaging is used to image various organs and areas of the body, and is one of the safest forms of imaging. However, ultrasound has not been used effectively during interventional medical diagnoses and treatment. One major limitation which prevents the conventional ultrasound system from providing effective imaging guidance for interventional medical diagnosis and treatment is that interventional catheters or laparoscopic surgery tools show very poor visualization in the B mode image due to the substantial impedance mismatch between the tissue and tools, especially when the tool has a small diameter or the field of interest is deep inside the body. In both of these cases, the reflected ultrasound wave from the tool is too weak so that it can hardly be detected.

Several different approaches have been developed to address the problem, including image processing, passive ultrasound markers, EM sensors, and optical sensors. However, these methods have their limitations due to the poor effectiveness, robustness, accuracy or high system complexity. Accordingly, there is a need in the art for improved ultrasound systems.

SUMMARY

A closed-loop ultrasound system according to an embodiment of the current invention includes an ultrasound receiver, an ultrasound transmitter at least one of integral with or at a predetermined position relative to the ultrasound receiver, and a trigger circuit configured to receive detection signals from the ultrasound receiver and to provide trigger signals to the ultrasound transmitter in response to received detection signals. The ultrasound transmitter is configured to transmit ultrasound energy in response to the trigger signals.

An ultrasound-active tool for use with an ultrasound imaging system according to an embodiment of the current invention includes a tool; an ultrasound receiver at least one of attached to or integral with the tool; an ultrasound transmitter at least one of attached to or integral with the tool, the ultrasound transmitter being at least one of integral with or at a predetermined position relative to the ultrasound receiver; and a trigger circuit configured to receive detection signals from the ultrasound receiver and to provide trigger signals to the ultrasound transmitter in response to received detection signals. The ultrasound transmitter is configured to transmit ultrasound energy in response to the trigger signals.

A system for interventional ultrasound imaging according to an embodiment of the current invention includes an ultrasound transducer for imaging a region of interest; an interventional tool including an active reflector element, the active reflector element configured to receive ultrasound pulses from the ultrasound transducer and transmit an ultrasound pulses back to the ultrasound transducer; and a processor for analyzing the ultrasound pulses to thereby form an image of the region of interest and active reflector element location.

A method for interventional tool tracking according to an embodiment of the current invention includes inserting an interventional tool into tissue, the interventional tool including an active reflector element to receive ultrasound pulses from the ultrasound transducer and transmit an ultrasound pulse back to the ultrasound transducer; collecting images of a region of interest with an ultrasound transducer; and analyzing the ultrasound pulses to thereby form an image of the region of interest and active reflector element location.

A method for determining in-plane indication for interventional tools according to an embodiment of the current invention includes inserting an interventional tool into tissue, the interventional tool including an active reflector element to receive ultrasound pulses from the ultrasound transducer and transmit ultrasound pulses back to the ultrasound transducer; collecting images of a region of interest with an ultrasound transducer; and analyzing the ultrasound pulses to thereby form an image of the region of interest and active reflector element location, wherein the active reflector element location is configured to be proportional to a received signal amplitude to indicate a best in-plane result.

A method of time reversal imaging for interventional tool tracking according to an embodiment of the current invention includes inserting an interventional tool into tissue, the interventional tool including an active reflector element to receive ultrasound pulses from the ultrasound transducer and transmit ultrasound pulses back to the ultrasound transducer; collecting images of a region of interest with an ultrasound transducer; analyzing amplitude and phase information from a signal received from the active reflector element; and reconstructing the incident wave front to determine an impulse response for the imaging region of interest. The impulse response provides a correction for the transmitting beam forming.

BRIEF DESCRIPTION OF THE DRAWINGS

Further objectives and advantages will become apparent from a consideration of the description, drawings, and examples.

DETAILED DESCRIPTION

Figure 1:
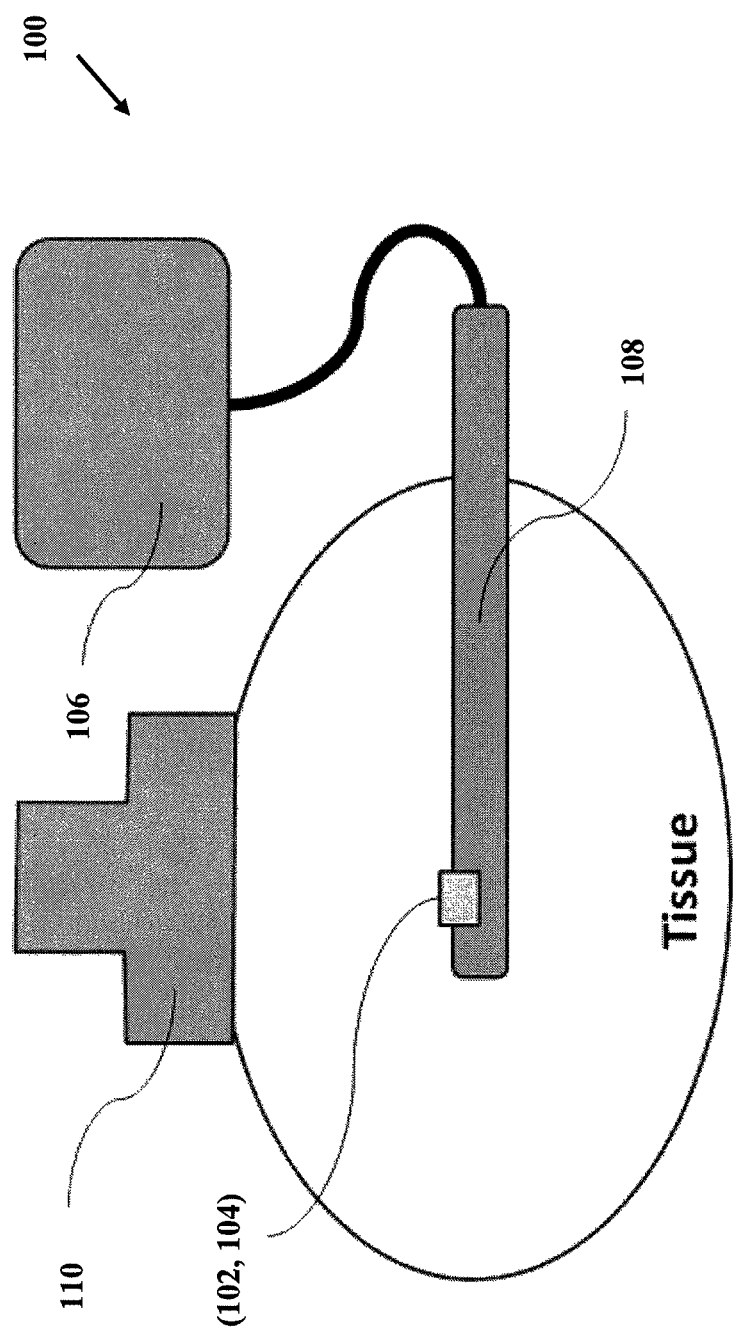
FIG. 1 is a schematic illustration of a closed-loop ultrasound system, an ultrasound-active tool, and a system for interventional ultrasound imaging according to some embodiments of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The terms "light" and "optical" are intended to have a broad meaning. They can include, but are not limited to, the visible regions of the electromagnetic spectrum. They can include nonvisible regions of the electromagnetic spectrum such as infrared and ultraviolet light, as well as visible regions.

The term "photoacoustic" is intended to have a broad definition which can be photons at any energy suitable for the particular application that deposit energy that generates an acoustic signal in a body of interest.

The term "body" refers general to a mass, and not specifically to a human or animal body. In some applications, the body of interest can be a human or animal organ, or a portion thereof.

The term "interstitial" means to be inserted into tissue, such as, but not limited to, a needle inserted into tissue with the inserted tip being surrounded by the tissue.

Some embodiments of the current invention provide an imaging guidance solution for interventional medical diagnosis and treatment based on the conventional B mode ultrasound imaging system. One major limitation which prevents conventional ultrasound systems from providing effective imaging guidance for interventional medical diagnosis and treatment is that interventional catheters or laparoscopic surgery tools show very poor visualization in the B mode image due to the substantial impedance mismatch between the tissue and tools, especially when the tool has small diameter or the field of interest is deep inside the body. In both of the two cases, the reflected ultrasound wave from the tool is too weak so as to be hardly detectable. Several different approaches have been developed to address the problem, including image processing, passive ultrasound markers, EM sensors, and optical sensors. However, these methods have their limitations due to the poor effectiveness, robustness, accuracy or high system complexity. Some embodiments of the current invention can provide a novel system to provide an effective interventional tool ultrasound imaging guidance solution with high accuracy and minimum system complexity. This can be implemented for artificial insemination (IUI, IVF and GIFT), Endocavity tools, HIFU/RF ablation catheters and other interventional surgery or diagnostic tools, for example. However, the broad concepts of the current invention are not limited to only these applications, and are not limited to only medical procedures. Other embodiments can be applied in conjunction with other uses of ultrasound.

In the context of medical applications, accurate medical tool tracking is a crucial task that directly affects the safety and effectiveness of many surgical and interventional procedures. Compared to CT and MRI, ultrasound based tool tracking has many advantages including low cost, safety, mobility and ease-of-use. One major limitation, however, that prevents conventional ultrasound imaging systems from providing effective tool tracking and guidance is the poor visualization of interventional tools. Therefore, some embodiments of the current invention provide an "active reflector" technique for interventional surgery tool guidance.

One or multiple ultrasound sensors and emitters work as the active elements. They can be either attached to the catheter and interventional tools, or the needle guide, styler, etc. which is detachable from the tool. A conventional medical ultrasound machine running in B mode can be used as the imaging device. In the operation, the catheter or interventional tool is inserted into the tissue, and the ultrasound imaging probe collects the image from outside of the body or organ. When ultrasound pulses generated by the imaging probe penetrate the tissue and reach the interventional tool, the sensor attached to it receives the signal and sends it to the electronics. The signal is then processed to trigger an ultrasound emitter element on the interventional tool to fire an ultrasound pulse back to the imaging probe. The signal receiving->processing->firing loop can be high speed optical and/or electrical components, so the entire loop delay can be down to the tens of nanosecond scale, which is negligible for ultrasound imaging. As a result, the active echo signal appears as a bright spot in the ultrasound B-mode image, indicating the element location. The echo time delay, frequency, amplitude, duration and temporal modulation can be controlled based on different applications. The active echo signal can either be displayed in the B-mode image, or be extracted by template or wavelet filtering methods for robot-assisted tool guidance, for example.

FIG. 1 provides a schematic illustration of a closed-loop ultrasound system 100 according to an embodiment of the current invention. The closed-loop ultrasound system 100 includes an ultrasound receiver 102, an ultrasound transmitter 104 at least one of integral with or at a predetermined position relative to the ultrasound receiver 102, and a trigger circuit 106 configured to receive detection signals from the ultrasound receiver 102 and to provide trigger signals to the ultrasound transmitter 104 in response to received detection signals. The ultrasound transmitter is configured to transmit ultrasound energy in response to the trigger signals.

Also shown in FIG. 1 is a surgical tool 108 to which at least a portion of the ultrasound receiver 102 and ultrasound transmitter 104 are attached. However, the general concepts of the current invention are not limited to this example. Depending of the application, the closed-loop ultrasound system 100 may or may not have portions attached to, or integrated with, a surgical tool or other type of tool. FIG. 1 also schematically illustrates an ultrasound probe 110 that is a portion of an ultrasound imaging system.

The trigger 106 can be included along with other electronics to provide signal detection, signal transmission, as well as other logical processing etc. Also, the ultrasound receiver 102 and ultrasound transmitter 104 can have one or more transducer elements located as is illustrated schematically in FIG. 1, as well as associated electronics which can be located along with the trigger 106, for example. However, the broad concepts of the current invention are not limited to specifically how the electronics associated with the various detection, transmission, time delay, etc. functions are packaged.

In some embodiments, at least one of the trigger circuit 106 or the ultrasound transmitter 104 can be configured to provide a predetermined delay between an ultrasound signal detected by the ultrasound receiver 102 and the transmission of ultrasound energy in response to the trigger signals. At such time delays, the transmission in response to the detection can be made to appear to be a reflection, but with modified reflection characteristics, such as, but not limited to, a greater intensity than an actual reflection. However, other embodiments can provide characteristics to the transmitted ultrasound energy, including, but not limited to time delays that are not fast to mimic reflection. An example of some such alternative embodiments will be described in more detail below.

In this configuration, one or multiple single element piezoelectric transducers can be attached near the tip of a catheter or surgical tool, for example. Each of the elements can work as an ultrasound sensor or emitter, or both. In the operation, the ultrasound pulses from the imaging probe propagate through the tissue and hit the receiving element on the catheter. The element turns the ultrasound signal to an electrical signal, which is amplified by the analog front end (AFE) circuit and triggers the high-voltage (HV) pulser. The high voltage pulse from the pulser is sent back to the element to generate ultrasound pulses. The transmitter (Tx) and receiver (Rx) elements can be the same PZT element, or separate ones located very close to each other, with different size, material and shape to optimize reception and transmission efficiency.

The PZT elements can be small tubes with a diameter and height of hundreds of microns to millimeter range. It can also be other shapes based on the catheter structure and application.

Figure 2:
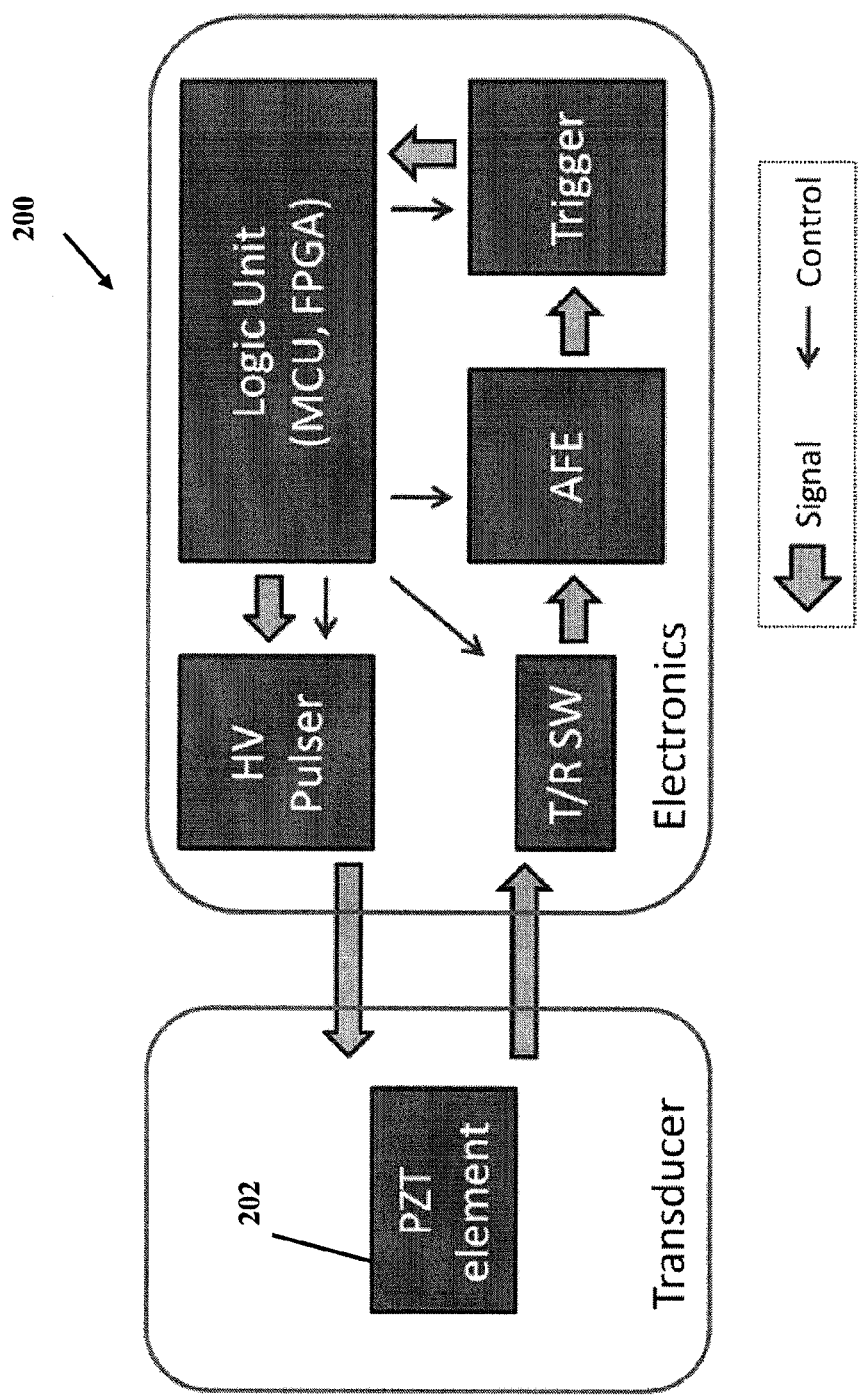
FIG. 2 is a schematic illustration of a closed-loop ultrasound system according to an embodiment of the current invention.
Figure 3:
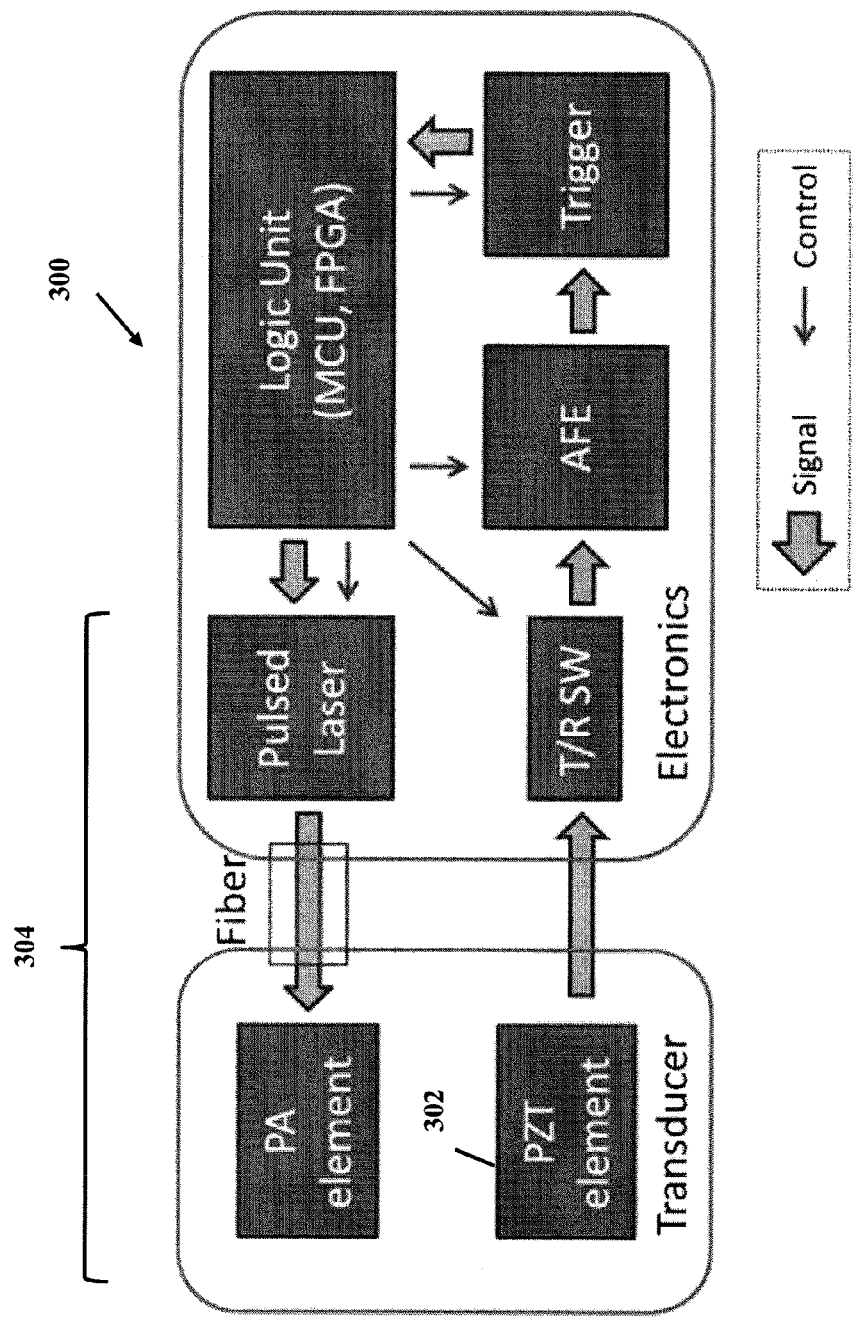
FIG. 3 is a schematic illustration of a closed-loop ultrasound system according to another embodiment of the current invention.
Figure 4:
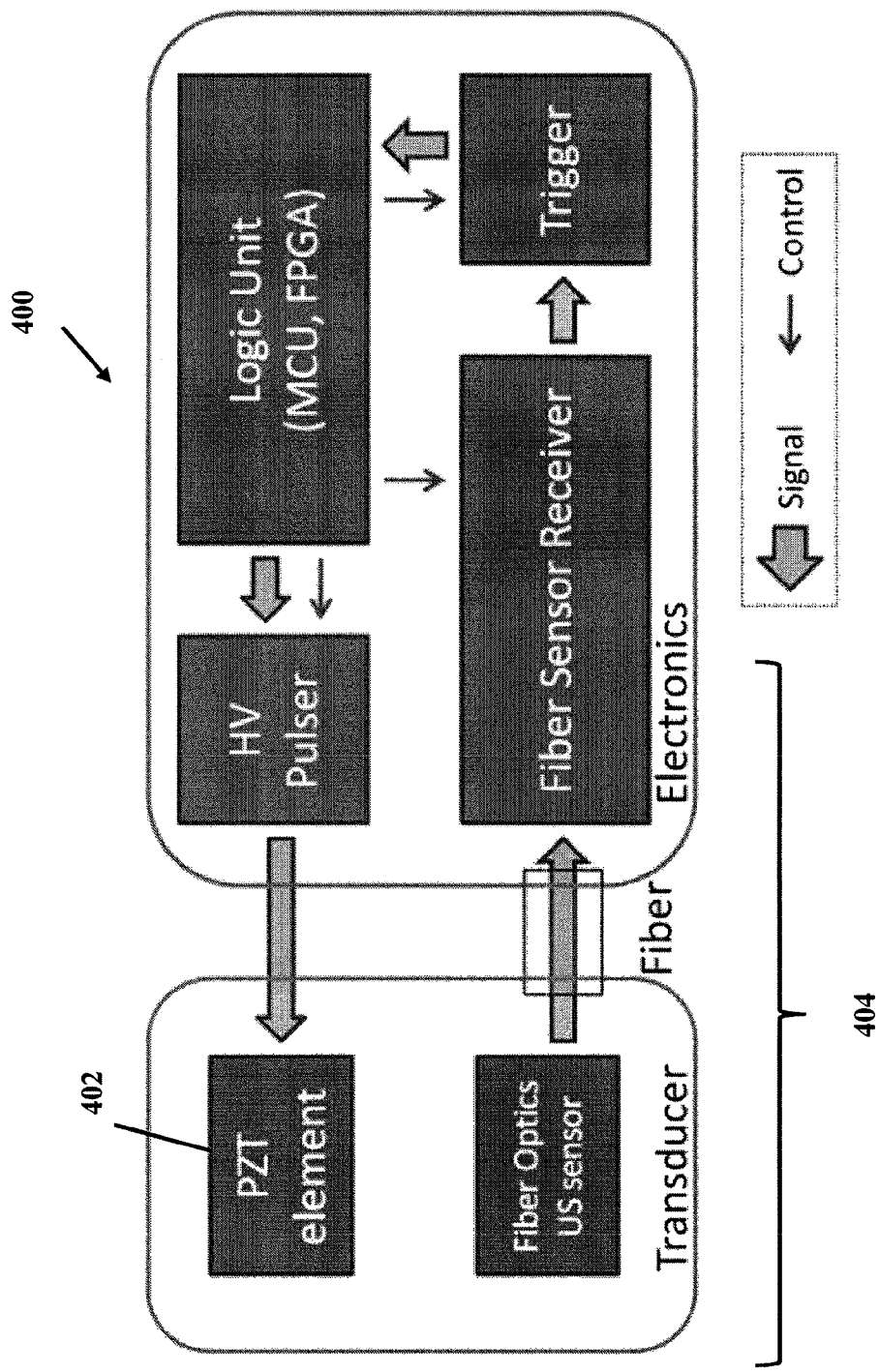
FIG. 4 is a schematic illustration of a closed-loop ultrasound system according to another embodiment of the current invention.

FIGS. 2, 3 and 4 provide schematic illustrations of closed-loop ultrasound systems 200, 300, 400, respectfully, according to three embodiments of the current invention. Each of the closed-loop ultrasound systems 200, 300, 400 includes at least one piezoelectric element 202, 302, 402 in ultrasound receiver 102 or ultrasound transmitter 104. Although the piezoelectric elements 202, 302, and 402 are indicated to be PZT elements as an example, the general concepts of the current invention are not limited to only that material. Piezoelectric elements from other materials may be used depending on the particular application.

In the closed-loop ultrasound system 200, the piezoelectric element 202 is used to both transmit and receive ultrasound signals. In the closed-loop ultrasound system 300, the piezoelectric element 302 is used to receive ultrasound signals, while transmission is by a photoacoustic transmitter 304. In the closed-loop ultrasound system 400, the piezoelectric element 402 is used to transmit ultrasound signals, while reception is by a fiber optic receiver 404.

Figure 5:
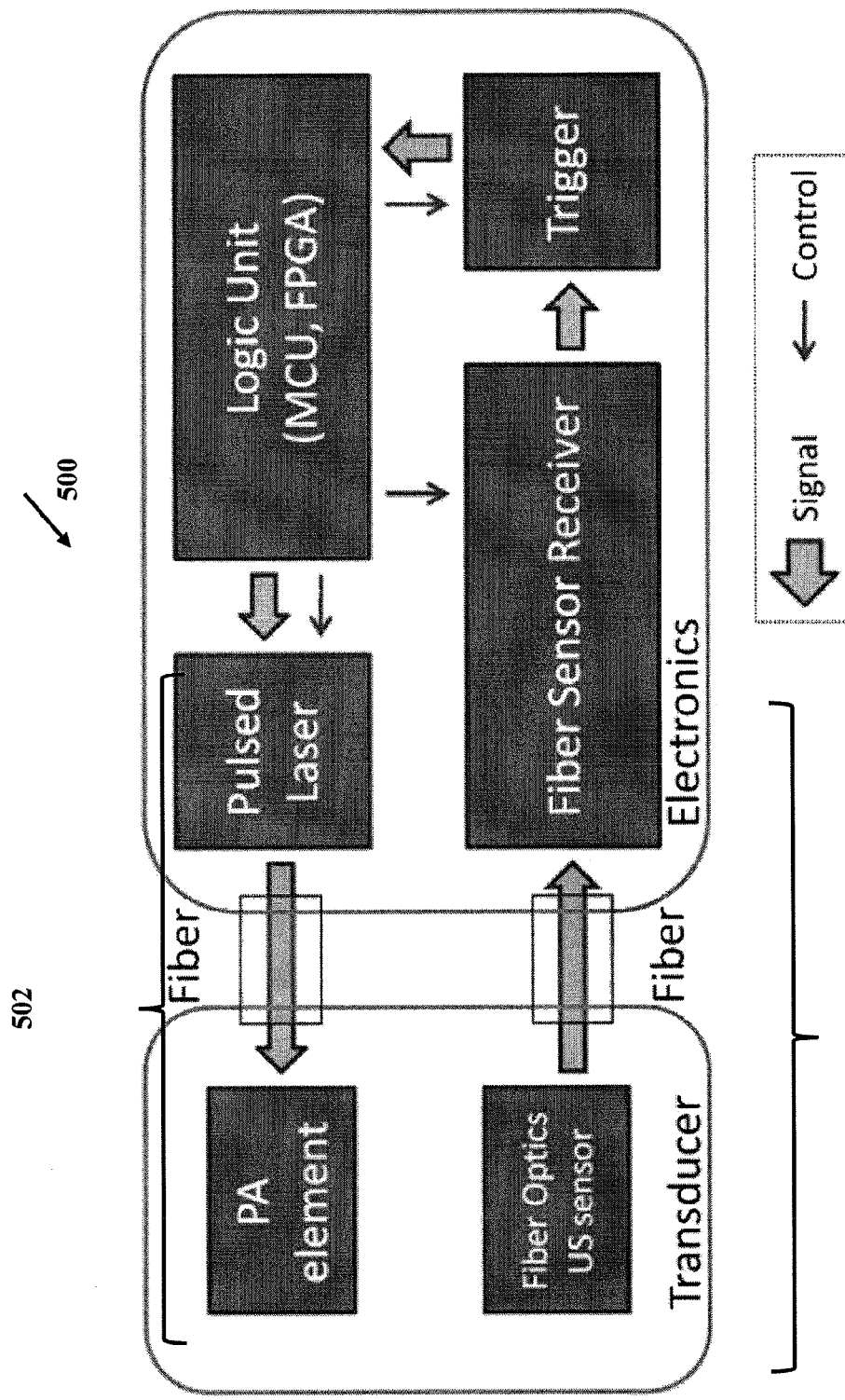
FIG. 5 is a schematic illustration of a closed-loop ultrasound system according to another embodiment of the current invention.

FIG. 5 provides a schematic illustration of a closed-loop ultrasound system 500 according to another embodiment of the current invention. In this embodiment, transmission is by a photoacoustic transmitter 502, and reception is by a fiber optic receiver 504. Although FIG. 5 shows the transmitter 502 and the receiver 504 as being separate elements in which they have separate optical fibers, in some embodiments, reception and transmission can be directed through the same optical fiber, as will be described in more detail below.

Figure 6:
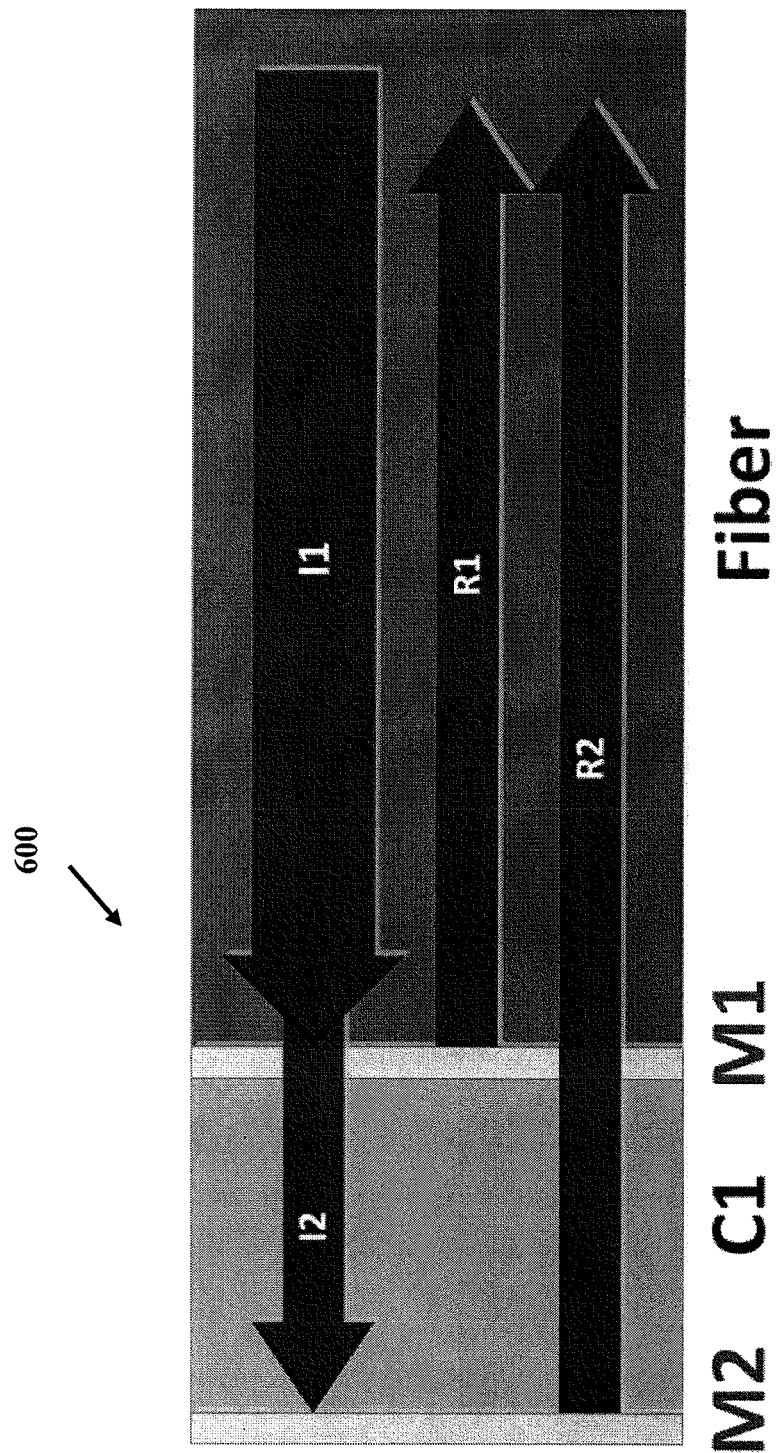
FIG. 6 is a schematic illustration of an optical sensor that can be used in a closed-loop ultrasound system according to another embodiment of the current invention.

FIG. 6 is a schematic illustration of an optical fiber sensor 600 to detect ultrasound signals according to an embodiment of the current invention. It can be used in the embodiments of FIGS. 4 and/or 5, and variations thereof, for example. The optical fiber sensor 600 is an optical fiber based Fabry-Perot interferometer. As shown in the figure, the laser beam I1 is sent through an optical fiber. At the fiber tip the reflective layer M1, M2 and the transparent layer C1 forms a Fabry-Perot interferometer. M1 is a partially reflective layer, at which the part of the laser beam R1 is reflected and the remaining beam I2 is transmitted. At the layer M2, I2 is reflected back. Both the beams R1 and R2 are reflected back, with a phase difference related to the thickness of C1. The overall backward reflection directly depends on the interference, in other words the phase delay between the beams, on the layer M1. When an ultrasound wave is incident on M2, the thickness of C1 changes with the sound wave, thus the phase delay between the two reflected beams changes as well. As a result, the ultrasound waveform can be detected by measuring the reflected laser beam amplitude.

Figure 7:
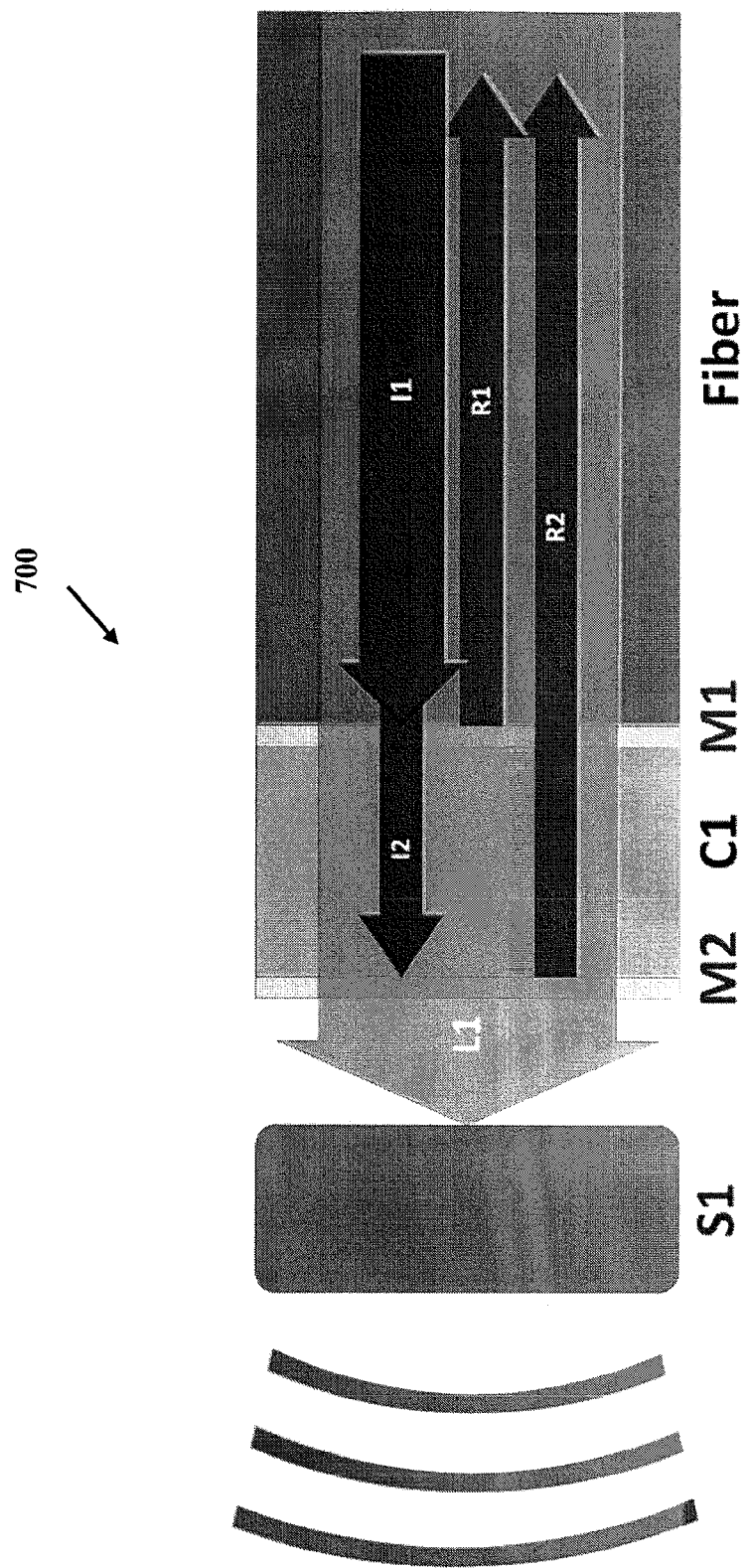
FIG. 7 is a schematic illustration of a portion of a photoacoustic transmitter that can be used in a closed-loop ultrasound system according to another embodiment of the current invention.

FIG. 7 is a schematic illustration of an embodiment that has an optical fiber for use with both transmission and detection. In this case the optical fiber sensor 700 is similar, or the same as, the optical fiber sensor 600, but the mirrors M1 and M2 are transparent to excitation light L1. It can be used in the embodiments of FIGS. 3 and/or 5, and variations thereof, for example. The ultrasound transmission uses the photoacoustic (PA) effect, while reception using a fiber based interferometer. Therefore, in this embodiment, the Tx and Rx can share the same optical fiber to further reduce the device footprint and complexity. As is shown in the FIG. 7, the fiber is used to guide both the detection laser beams (I1, I2, R1, R2) and the PA excitation beam (L1). The PA beam has a wavelength of $\lambda_1$ and the detection beam has a wavelength of $\lambda_2$. The mirrors M1 and M2 are designed to be transparent for $\lambda_1$ and reflective for $\lambda_2$. (The term "transparent" is intended to mean that a sufficient amount of light L1 passes through to provide an adequate photoacoustic signal for the particular application.) As a result, the PA beam will be output from the fiber tip and absorbed by the PA element S1. S1 absorbs the laser energy and generates a photoacoustic pulse.

Figure 8:
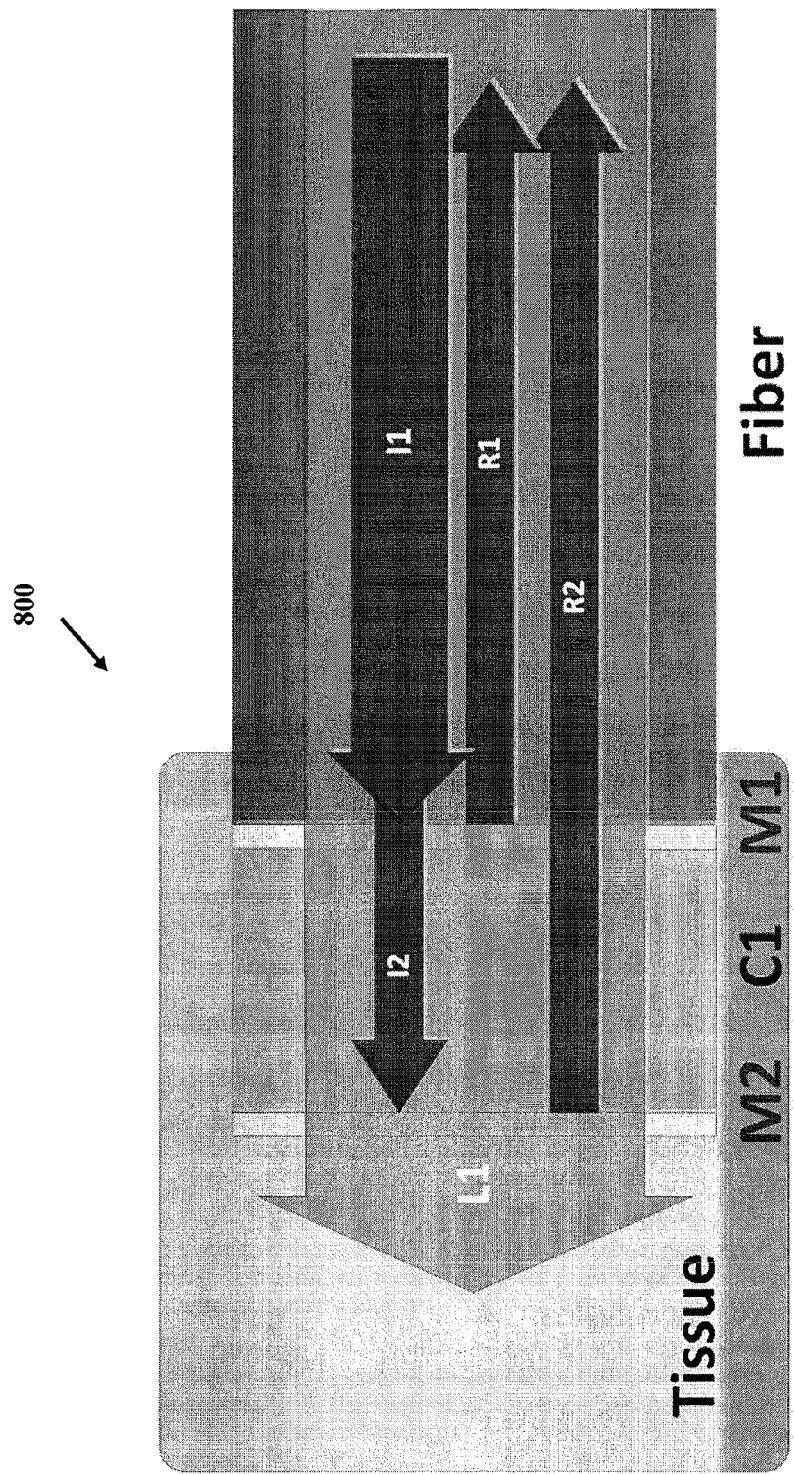
FIG. 8 is a schematic illustration of a portion of a photoacoustic transmitter that can be used in a closed-loop ultrasound system according to another embodiment of the current invention.

FIG. 8 is a schematic illustration of another embodiment that has an optical fiber for use with both transmission and detection. In this case the optical fiber sensor 800 is similar, or the same as, the optical fiber sensor 600, but the mirrors M1 and M2 are transparent to excitation light L 1. This can be similar or the same as the embodiment of FIG. 7, but without photoacoustic element S1. Depending on the applications, the PA beam can be directly delivered to the tissue. The laser energy is absorbed by the tissue and generates photoacoustic signals. Consequently, in this case, the PA element S1 is not needed.

Figure 9:
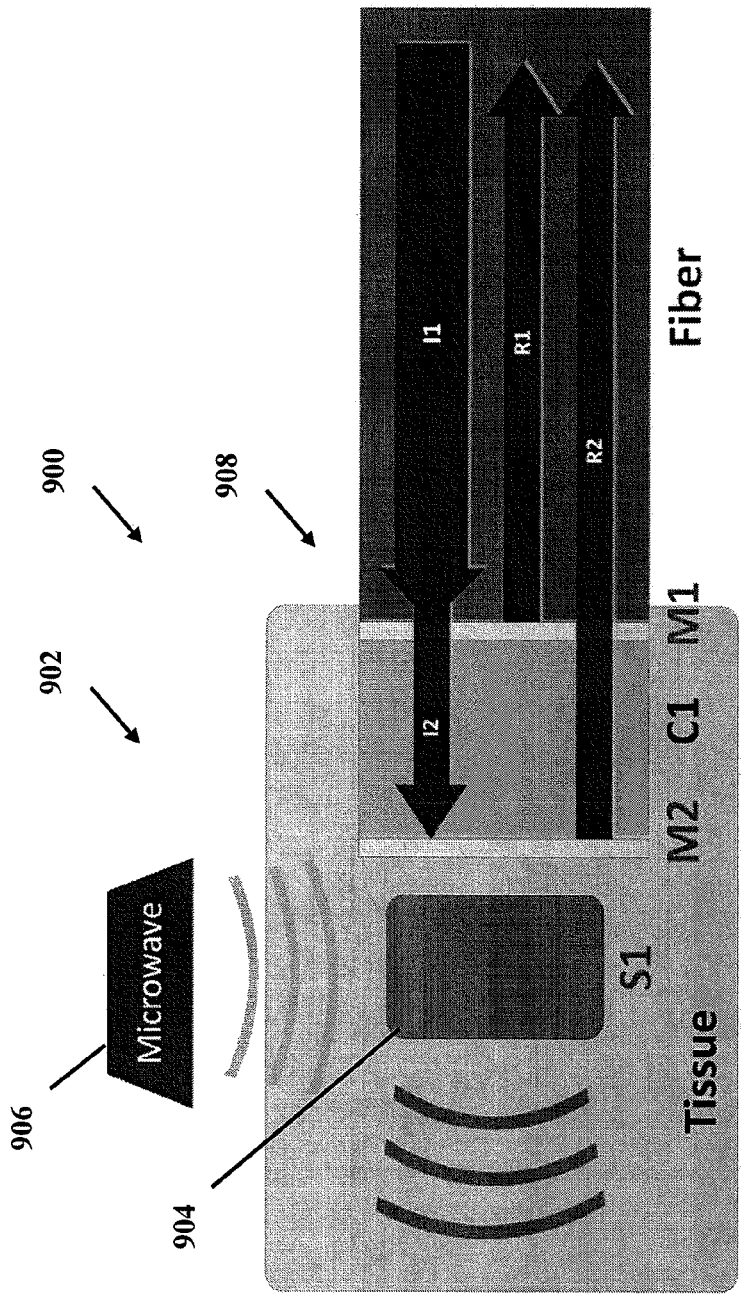
FIG. 9 is a schematic illustration of a portion of a thermoacoustic transmitter and optical sensor that can be used in a closed-loop ultrasound system according to another embodiment of the current invention.

FIG. 9 is a schematic illustration of a portion of a closed-loop ultrasound system 900 according to another embodiment of the current invention. The closed-loop ultrasound system 900 includes an ultrasound transmitter 902 that includes a thermoacoustic element 904 and a microwave transmitter 906. The ultrasound receiver 908 can be an optical receiver such as, but not limited to, that of FIG. 6. However, piezoelectric and/or other ultrasound receivers can alternatively be used in other embodiments. In this configuration, a pulsed microwave generator outside the tissue can send microwave pulses to the target region, the thermoacoustic element 904 absorbs the microwave energy and generates thermoacoustic pulses.

Figure 10:
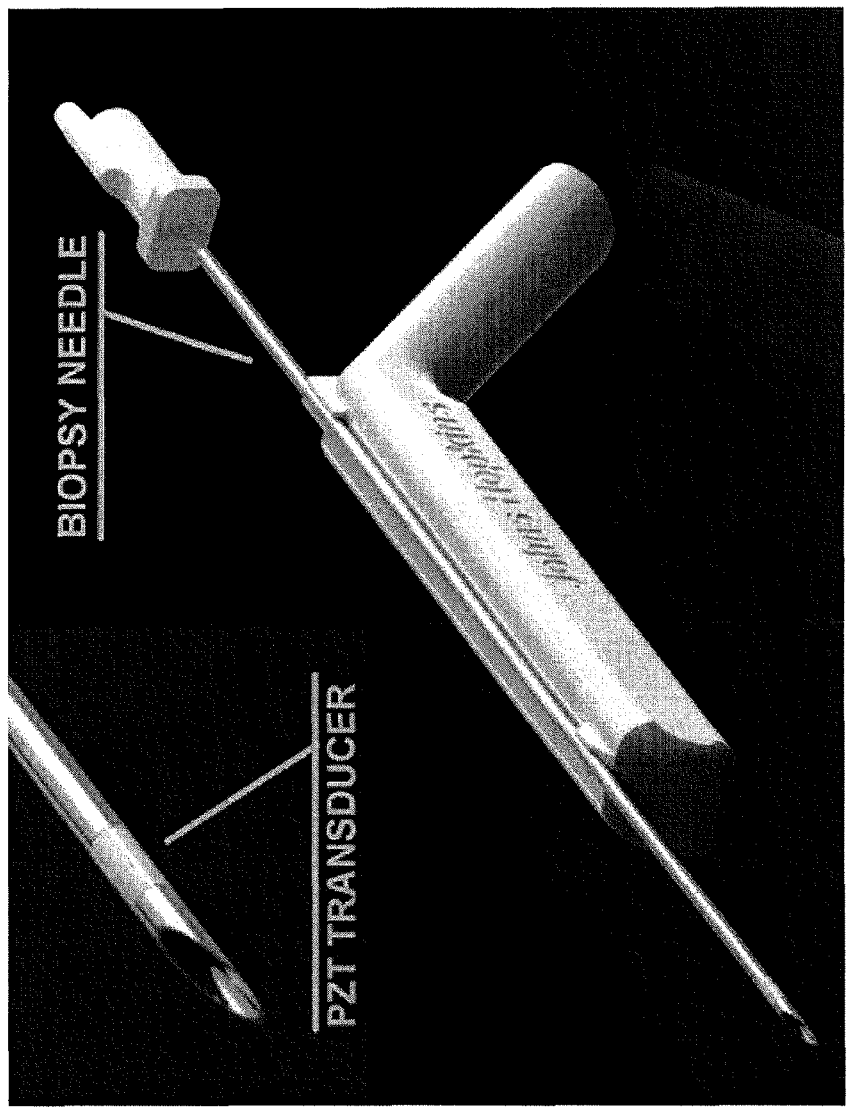
FIG. 10 shows an example of an ultrasound-active tool according to an embodiment of the current invention.

In some embodiments of the current invention, an ultrasound-active tool for use with an ultrasound imaging system can include a closed-loop ultrasound system attached to or integrated with a tool. The tool can be, but is not limited to, a surgical tool. FIG. 10 shows an example of a biopsy needle that has one or more PZT transducers that are part of a closed-loop system according to an embodiment of the current invention. The concepts of the current invention are not limited to this particular example. In some embodiments, the surgical tool can be, but is not limited to, a needle, a surgical cannula, an endoscope, a trocar, a catheter, an ablation tool, a grasping tool.

Figure 11:
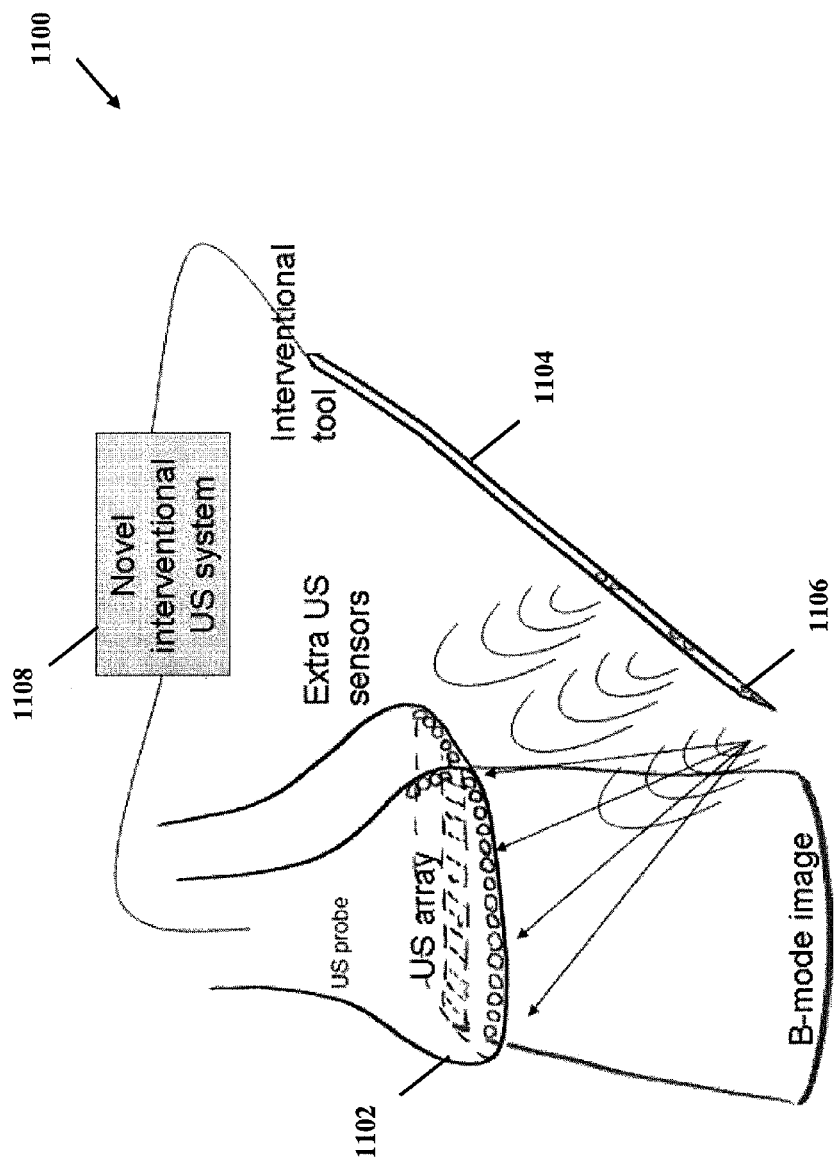
FIG. 11 is a schematic illustration of a system for interventional ultrasound imaging according to some embodiments of the current invention.

FIG. 11 is a schematic illustration of a system for interventional ultrasound imaging 1100 according to an embodiment of the current invention that includes an ultrasound transducer 1102 for imaging a region of interest, an interventional tool 1104 including an active reflector element 1106, the active reflector element configured to receive ultrasound pulses from the ultrasound transducer 1104 and transmit an ultrasound pulse back to the ultrasound transducer 1104, and a processor 1108 for analyzing the ultrasound pulses to thereby form an image of the region of interest and the active reflector element location.

Figure 12:
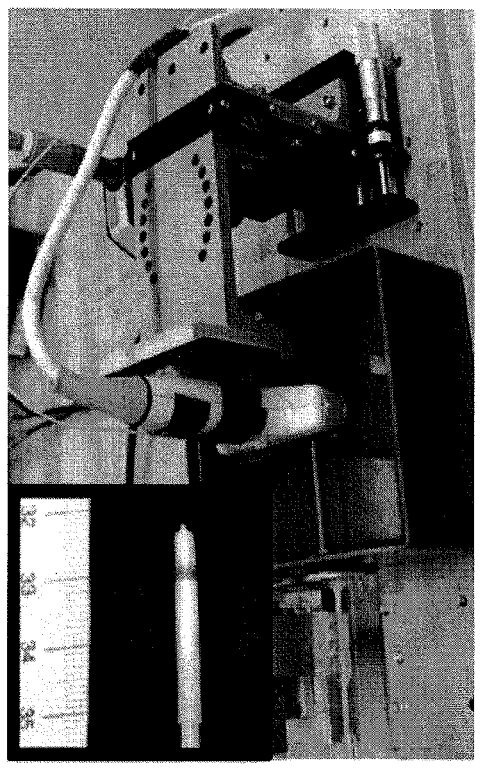
FIG. 12 is a schematic illustration and partial image of a system for interventional ultrasound imaging according to another embodiment of the current invention.
Figure 12:
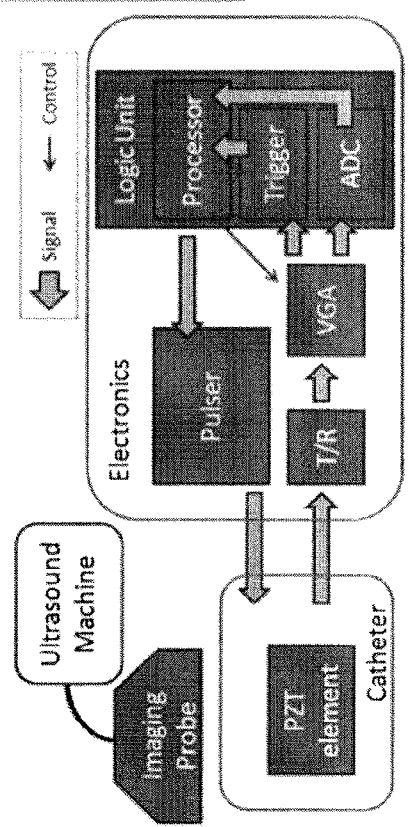

FIG. 12 is a schematic illustration (left) of a system for interventional ultrasound imaging according to another embodiment of the current invention. An image of a portion of the system is shown on the right-hand side of FIG. 12.

The following examples will describe some more details of some embodiments of the current invention. However, the broad concepts of the current invention are not limited only to these particular examples.

EXAMPLES

The following describes some methods according to some embodiments of the current invention. The general concepts of the current invention are not limited to these examples.
Method 1: Interventional Tool Tracking The tool position tracking, usually the tool tip position tracking, can be done by implementing a single active reflector element on the interventional tool. As described above, the element effectively "reflects" the imaging pulses from the imaging probe with ignorable delay, but much higher amplitude. It creates a bright spot in a conventional B mode view. The spot represents the element location in the ultrasound image.

Figure 13:
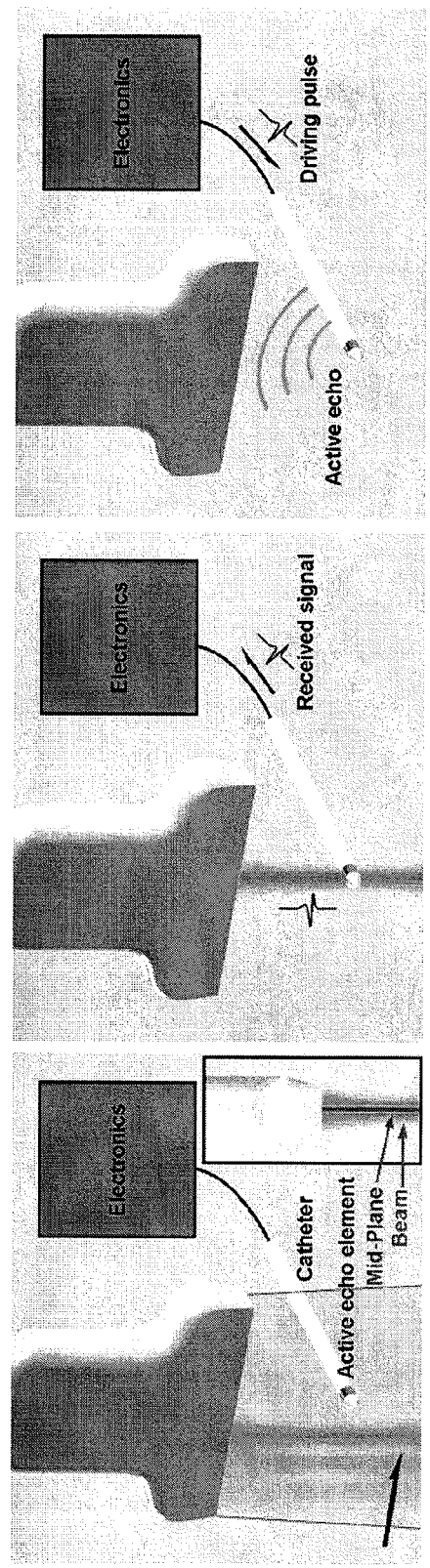
FIG. 13 is a schematic illustration to help explain a method according to an embodiment of the current invention.

The tool orientation tracking can be done by using two or more active "reflector" elements. Based on the same principle, each element can create one spot in the B mode image. The multiple spots represent the shape and orientation of the catheter in the tissue. This method can be especially useful when the tool is flexible, such as, but not limited to, application #1 described below for B mode image-guided artificial insemination.
Method 2: Precision In-Plane Indication One unique feature of a B mode ultrasound image is that the imaging plane is "thick", i.e. the imaging ultrasound pulse has a beam width of several millimeters. The B mode image is actually the sum of all the scattering signals within that width. However, the beam intensity is higher at the center, and lower near the edge, and usually has a Gaussian distribution (FIG. 13). This unique feature can permit an active reflector device according to an embodiment of the current invention to precisely indicate if the tool is in-plane or out-plane. When the active reflector element is moved from one side to the other side of the beam, the received signal amplitude goes from low to high, and back to low again. The highest signal indicates that the element is right at the center of the beam. This information can be feed back to the operator by different methods. For example, the active reflection power can be configured to be proportional to the received signal amplitude, so the operator can adjust the tool for the maximum spot brightness in the B mode image to get the best in-plane result. The system can also be configured to fire the active reflection pulse periodically such that the period is proportional to the received signal amplitude. As a result, the operator will see the spot blinking in the B mode image, and the blinking frequency represents how far the element is from the center of the imaging plane. In another example, the graphic user interface may have a level bar indicating how far the element is from the plane center.
Method 3: Time Reversal Imaging In addition to a tracking function, the active reflector system can also be used to improve the ultrasound image quality by a time reversal imaging method. The single or multiple, elements on the interventional tool can work as point ultrasound sources inside the field of interest. The imaging array receives the signal from these point sources. By analyzing the amplitude and phase information of the received signal, the incident wave front can be reconstructed, thus the impulse response of the imaging region tissue can be found. The impulse response provides a correction for the Tx beam forming, and improves the focusing precision. Therefore, better image quality can be provided by this method.
Method 4: Frequency and Pattern Based Active Marker Extraction In some applications it will be desired to extract the position marker generated by the active reflector from the B mode image. For example, by extracting the position information, a colored marker can be injected to the B mode display to improve the visualization. Another example is that the quantified position information can be used for the robot assisted tool guidance.

Figure 14:
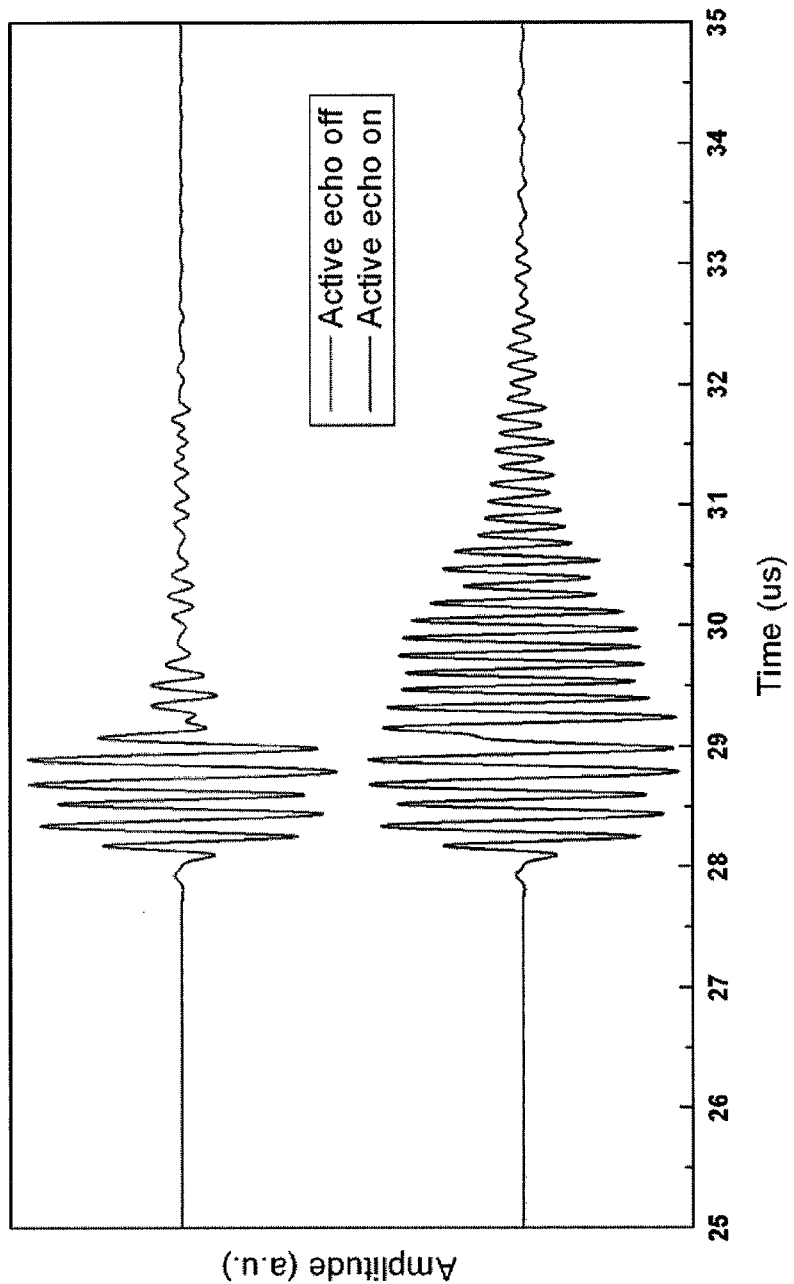
FIG. 14 shows the same post beamforming RF line with and without active reflected pulse. The active reflection pulse has slightly higher frequency than the imaging pulse.

One method to extract an active marker is based on the frequency extraction. The active reflector fires pulses with different frequency from the imaging pulses from the image probe. For example, the active reflected pulse has higher frequency than that of the image pulses. As a result, the received post beamforming RF lines will looks like the FIG. 14.

Another method to extract the active marker is based on the modulation of the active reflection pulse. We can modulate the ringing tail with a unique temporal envelop pattern. In the B mode image, we will see this pattern in gray scale, like a bar code. Image processing algorithms can be developed to extract this pattern from the B mode image, and find the marker position. This method can be useful for systems in which post beamforming RF data is not accessible.

Figure 15:
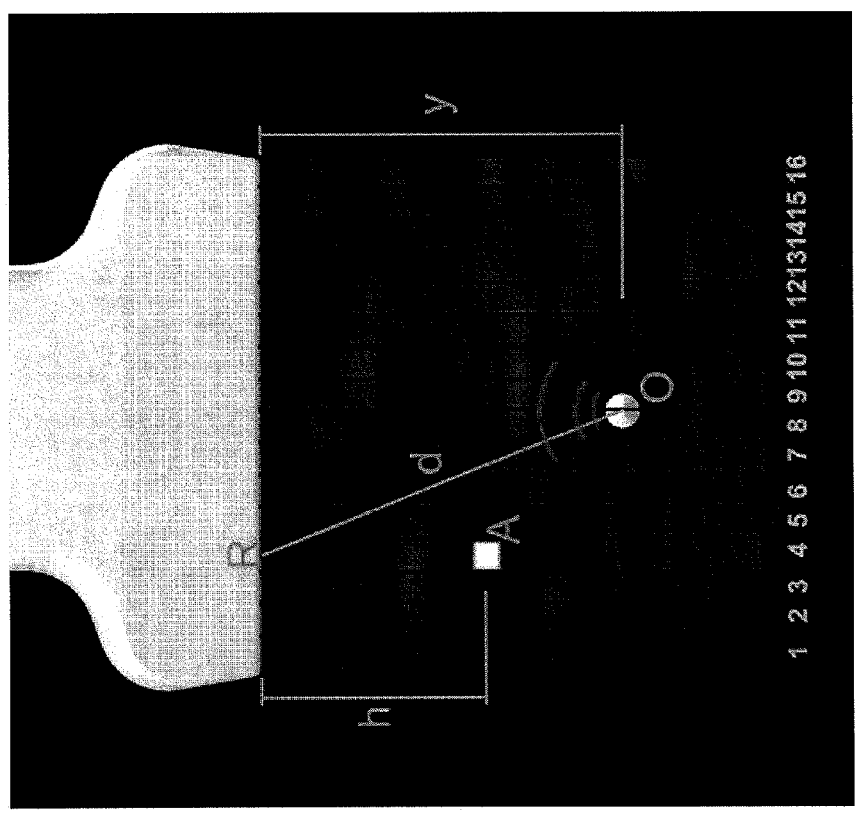
FIG. 15 helps explain a method of arbitrary pattern injection according to another embodiment of the current invention.

In this method, using a single active element system, either piezoelectric, optical or microwave based configuration, an arbitrary virtual pattern can be injected to the B-mode image. A B-mode image is formed by a series of A-mode lines. Each A-mode line is formed by the signal send and received from a group of elements. These A-mode lines are acquired in series. As shown in FIG. 15. Suppose the B mode image is composed of 16 A-mode lines, the normal distance from the active echo element to the probe is y. To generate a virtual spot on the point A, an ultrasound pulse should be received by the probe when the A-mode line #4 is being acquired, with a delay of $$t_{delay} = \frac{2 \times h}{c},$$

where c is the speed of sound in this medium. The ultrasound pulse is generated from the active echo element at position O, the distance between O and the center of the imaging elements R is d. The time for sound to travel from O to R is ttravel=d/c. So the timing that the element should send an ultrasound pulse is:

$$t = t_{delay} - t_{travel} = \frac{2 \times h - d}{c}.$$

In other words, if the active echo element fires an ultrasound pulse t seconds after the probe starts acquiring the A mode line #4, a bright spot will show up at position A in the B-mode image. In this setup, we need the line trigger signal from the ultrasound machine to get the start timings of each A-mode line acquisition.

Having these spots as "pixels", arbitrary patterns can be formed and injected to the image. But one problem remains in the previous statement: the distance between O and R is unknown in the real case. However, since the linear array size, the total number of A-mode lines, and the speed of sound are known parameters, d can be automatically found by the system. In the FIG. 15, the active element may receive imaging pulses when the probe is acquiring the nearby A-lines, depending on the receiver sensitivity. However, only line #8 or #9 gives the minimum delay time t-receive between the line triggering and the signal receiving, because it has the shortest sound traveling distance. So the system knows that the element is located between the line #8 and #9, with a normal distance y=c*t-receive. Because the array size and number of A-lines are known, d can be found.

Compared to conventional ultrasound tracking methods, i.e., the beam steering/image processing method, passive ultrasound markers, EM sensors and optical sensors, some embodiments of the current invention can provide the following novel features:

High accuracy. In the active tracking methods (EM and optical), the EM tracking technology with the conventional ultrasound imaging provides a localization accuracy of 5 mm. The optical tracking accuracy is even worse than the EM tracking method in many cases. Our active reflector system can provide a localization accuracy of less than half millimeter.

Standalone operation, high compatibility. The current active tracking methods, including the EM and optical tracking, or the beam steering/imaging processing approach, all require a specialized or modified ultrasound imaging system or software. Some embodiments of the current invention can work as standalone equipment, compatible with most commercialized ultrasound imaging equipment, such that no modification is needed.

Very small footprint, flexible configuration, complex EM environment compatibility, easy to implement. The EM tracking sensor is usually a micro-solenoid with a diameter of 1~2 mm and length of 5~10 mm. The sensor is a solid piece, which means it has to be placed at the center of the catheter, and it is impossible to pass anything through it. The EM tracker is very sensitive to the EM environment. Any metal pieces within the EM field range may greatly reduce its localization accuracy. The EM tracking system also requires an EM filed generator, which is a bulky device, being placed close to the sensor. The optical tracking technology can only apply to rigid body surgery tools, and requires direct line of sight from the camera to the tool. The active reflector transducer, according to some embodiments of the current invention, is a small piece of ultrasound element (PZT element in some cases). The size can easily be less than 1 mm, and the shape is very flexible to fit different tools and applications. It is naturally immune to the environmental magnetic interference. The only component added to the conventional operation setup is the ultrasound element; no bulky device such as an EM generator or stereo camera in the operation region.

Easy to use. Either EM tracking or optical tracking method requires calibration. The active reflector transducer, according to some embodiments of the current invention does not require a calibration process.

Single tracking, no registration. In either the EM or the optical tracking method, both the surgery tool and the ultrasound probe need to be tracked, and then the relative position information must be registered to the ultrasound image. With the active reflector system, according to some embodiments of the current invention, only the surgery tool needs to be tracked, and the localization marker is directly injected to the ultrasound field, thus displayed in the B mode image or extracted by the software. No registration is needed.

Low cost. The EM tracker system is composed of EM sensors, EM generator and the supporting electronics, which is too expensive for it to be disposable. The optical tracker system is composed of optical markers, stereo camera and the image processing system. Our active reflector system is composed of ultrasound elements and supporting electronics, does not contain expensive components; and the system manufacturing cost can be less than $100. The sensor (ultrasound element) cost is only a few dollars in mass production, which enables applications for disposable surgery tools.

This system can be used in any interventional catheter, needle or tool that requires imaging guidance. The following are several examples of how an active reflector can be implemented according to some embodiments of the current invention and improve the medical treatment process.

Application 1: B Mode Imaging Guided Artificial Insemination (AI)

Current intrauterine insemination (IUI) has a success rate of less than 20%. In vitro fertilisation (IVF) improves the rate to 40~50%, however, it is very costly and time consuming due to the complicated process and special facility requirements. Gamete Intrafallopian Transfer (GIFT) is a method that combines the advantages of IUI and IVF. However, it is not widely used because of the lack of an effective catheter guidance solution. Doctors have to open the patient and inject the sperm to an ovary from outside by a needle, which makes the treatment very complex and intrusive. The active reflector tracking system can provide a low cost, less complex and effective imaging guidance solution to the AI process. By including an active reflector element at the tip of the soft catheter, the operator gets a clear view of the catheter location in a B mode image, and guides the catheter to through the vagina, uterus and into the fallopian tube, to then inject the sperm. This makes the AI process simple and noninvasive.

Application 2: Endocavity SPECT Tool Real Time B Mode Imaging Guidance

Miniature SPECT sensor arrays have recently been developed and implemented into endocavity imaging tools for prostate cancer diagnosis. These tools have very poor B mode image visualization, which makes the image registration very difficult in multimodality imaging. Multiple active reflector elements can be included in the endocavity SPECT tool. In the B mode ultrasound image, each of these elements generates a bright spot, which represents the element location. By tracking these spots one can find the tool location and orientation.

Application 3: HIFU/RF Ablation Catheter, Interventional Surgery Tool and Biopsy Needle Real Time B Mode Imaging Guidance HIFU/RF ablation catheters, interventional surgery tools and biopsy needles have poor visualization in the ultrasound image. An active reflector element can be included to indicate the tool location in B mode images. This can improve the operation accuracy and safety.

These are some of the possible applications. However, the general concepts of the current invention are not limited to these examples.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A closed-loop ultrasound system, comprising:
an ultrasound receiver configured to receive ultrasound signals from an external transmitter;
an ultrasound transmitter at least one of integral with or at a predetermined position relative to said ultrasound receiver; and
a trigger circuit configured to receive detection signals from said ultrasound receiver and to provide trigger signals to said ultrasound transmitter in response to received detection signals,
wherein said ultrasound transmitter is configured to transmit ultrasound energy to be received by an external receiver in response to said trigger signals.

2. A closed-loop ultrasound system according to claim 1, wherein at least one of said trigger circuit or said ultrasound transmitter is configured to provide a predetermined delay between an ultrasound signal detected by said ultrasound receiver and transmitting ultrasound energy in response to said trigger signals.

3. A closed-loop ultrasound system according to claim 1, wherein at least one of said ultrasound receiver and said ultrasound transmitter comprises a piezoelectric element.

4. A closed-loop ultrasound system according to claim 1, wherein each of said ultrasound receiver and said ultrasound transmitter comprises a piezoelectric element.

5. A closed-loop ultrasound system according to claim 1, wherein said ultrasound receiver and said ultrasound transmitter comprise a piezoelectric element for both reception and transmission modes.

6. A closed-loop ultrasound system according to claim 1, wherein said ultrasound transmitter is a photoacoustic transmitter.

7. A closed-loop ultrasound system according to claim 6, wherein said photoacoustic transmitter comprises a photoacoustic element that converts absorbed optical energy into acoustic energy.

8. A closed-loop ultrasound system according to claim 6, wherein said ultrasound receiver comprises a piezoelectric element.

9. A closed-loop ultrasound system according to claim 6, wherein said ultrasound receiver comprises an optical ultrasound detector.

10. A closed-loop ultrasound system according to claim 9, wherein said optical ultrasound detector comprises an optical fiber having a Fabry-Perot element.

11. A closed-loop ultrasound system according to claim 10, wherein said photoacoustic transmitter comprises a second optical fiber.

12. A closed-loop ultrasound system according to claim 10, wherein said optical fiber provides a common optical waveguide for both said photoacoustic transmitter and said optical ultrasound detector.

13. A closed-loop ultrasound system according to claim 1, wherein said ultrasound receiver comprises an optical ultrasound detector.

14. A closed-loop ultrasound system according to claim 13, wherein said optical ultrasound detector comprises an optical fiber having a Fabry-Perot element.

15. A closed-loop ultrasound system according to claim 14, wherein said ultrasound transmitter comprises a piezoelectric element.

16. A closed-loop ultrasound system according to claim 14, wherein said ultrasound transmitter comprises a thermoacoustic element and a microwave transmitter.

17. A closed-loop ultrasound system according to claim 1, wherein said ultrasound transmitter comprises a thermoacoustic element and a microwave transmitter.

18. An ultrasound-active tool for use with an ultrasound imaging system, comprising:
a tool;
an ultrasound receiver at least one of attached to or integral with said tool and configured to receive ultrasound signals from an external transmitter;
an ultrasound transmitter at least one of attached to or integral with said tool, said ultrasound transmitter being at least one of integral with or at a predetermined position relative to said ultrasound receiver; and
a trigger circuit configured to receive detection signals from said ultrasound receiver and to provide trigger signals to said ultrasound transmitter in response to received detection signals,
wherein said ultrasound transmitter is configured to transmit ultrasound energy to be received by an external receiver in response to said trigger signals.

19. An ultrasound-active tool according to claim 18, wherein at least one of said trigger circuit or said ultrasound transmitter is configured to provide a predetermined delay between an ultrasound signal detected by said ultrasound receiver and transmitting ultrasound energy in response to said trigger signals.

20. An ultrasound-active tool according to claim 18, wherein at least one of said ultrasound receiver and said ultrasound transmitter comprises a piezoelectric element.

21. An ultrasound-active tool according to claim 18, wherein each of said ultrasound receiver and said ultrasound transmitter comprises a piezoelectric element.

22. An ultrasound-active tool according to claim 18, wherein said ultrasound receiver and said ultrasound transmitter comprise a piezoelectric element for both reception and transmission modes.

23. An ultrasound-active tool according to claim 18, wherein said ultrasound transmitter is a photoacoustic transmitter.

24. An ultrasound-active tool according to claim 23, wherein said photoacoustic transmitter comprises a photoacoustic element that converts absorbed optical energy into acoustic energy.

25. An ultrasound-active tool according to claim 23, wherein said ultrasound receiver comprises a piezoelectric element.

26. An ultrasound-active tool according to claim 23, wherein said ultrasound receiver comprises an optical ultrasound detector.

27. An ultrasound-active tool according to claim 26, wherein said optical ultrasound detector comprises an optical fiber having a Fabry-Perot element.

28. An ultrasound-active tool according to claim 27, wherein said photoacoustic transmitter comprises a second optical fiber.

29. An ultrasound-active tool according to claim 27, wherein said optical fiber provides a common optical waveguide for both said photoacoustic transmitter and said optical ultrasound detector.

30. An ultrasound-active tool according to claim 18, wherein said ultrasound receiver comprises an optical ultrasound detector.

31. An ultrasound-active tool according to claim 30, wherein said optical ultrasound detector comprises an optical fiber having a Fabry-Perot element.

32. An ultrasound-active tool according to claim 30, wherein said ultrasound transmitter comprises a piezoelectric element.

33. An ultrasound-active tool according to claim 30, wherein said ultrasound transmitter comprises a thermoacoustic element and a microwave transmitter.

34. An ultrasound-active tool according to claim 18, wherein said ultrasound transmitter comprises a thermoacoustic element and a microwave transmitter.

35. An ultrasound-active tool according to claim 18, wherein said tool is a surgical tool.

36. An ultrasound-active tool according to claim 35, wherein said surgical tool is one of a needle, a surgical cannula, an endoscope, a trocar, a catheter, an ablation tool, or a grasping tool.

* * * * *

UNITED STATES PATENT AND TRADEMARK OFFICE
CERTIFICATE OF CORRECTION

| | | |
|---|---|---|
| PATENT NO. | : 9,636,083 B2 | |
| APPLICATION NO. | : 13/943649 | |
| DATED | : May 2, 2017 | |
| INVENTOR(S) | : Emad M. Boctor et al. | |

It is certified that error appears in the above-identified patent and that said Letters Patent is hereby corrected as shown below:

In the Inventors item (72), replace "Pezhman Forought, Baltimore, MD (US)"
with -- "Pezhman Foroughi, Baltimore, MD (US)" --

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*